United States Patent [19]

Ebihara et al.

[11] 4,149,894

[45] Apr. 17, 1979

[54] PROCESS FOR PRODUCING AN APATITE POWDER HAVING IMPROVED SINTERABILITY

[75] Inventors: Masatomi Ebihara; Masahide Inoue; Tsuneo Hidaka, all of Tsurugashima, Japan

[73] Assignee: Asahi Kogaku Kogyo Kabushiki Kaisha, Tokyo, Japan

[21] Appl. No.: 887,913

[22] Filed: Mar. 17, 1978

Related U.S. Application Data

[62] Division of Ser. No. 802,856, Jun. 2, 1977, Pat. No. 4,113,500.

[30] Foreign Application Priority Data

Jun. 2, 1976 [JP] Japan ................................. 51/64184

[51] Int. Cl.² ...................... C01B 25/32; C04B 35/00
[52] U.S. Cl. .................................... 106/39.5; 106/35; 106/45; 106/286.6; 106/286.2; 423/308; 423/309
[58] Field of Search ............... 106/286, 39.5, 45, 306; 423/307, 308-311

[56] References Cited

U.S. PATENT DOCUMENTS

| 3,379,541 | 4/1968 | Tuvell | 106/286 X |
| 3,893,841 | 7/1975 | Nijhawan | 106/45 |
| 4,097,935 | 7/1978 | Jarcho | 106/39.5 X |

OTHER PUBLICATIONS

Publicly disclosed Japanese Patent Appl'n No. 51-40400, May 4, 1976 and (43 pages of English Translation).

Neuman, W. F. et al., "Synthetic Hydroxyapatite Crystals, IV. Magnesium Incorporation"-Chem. Abstracts 75 (1971) p. 324, item 68591x Aoki, H. et al. "Formation of Calcium Phosphates in Aqueous Solution at 37° C."-Report of the Institute for Medical & Dental Eng. 7 (1973) pp. 107-111 (and English translation).

Primary Examiner—Helen McCarthy
Attorney, Agent, or Firm—Sughrue, Rothwell, Mion, Zinn and Macpeak

[57] ABSTRACT

A sintered apatite body obtained by molding and sintering an apatite powder, $Ca_5(PO_4)_3OH$, containing 0.01 to 20% by weight of $(Ca,Mg)_3(PO_4)_2$. The sintered apatite body has high mechanical strength and good affinity with living tissues and cells, and is suitable as medical implant materials such as prosthetic teeth or bones.

4 Claims, No Drawings

PROCESS FOR PRODUCING AN APATITE POWDER HAVING IMPROVED SINTERABILITY

This is a Division of application Ser. No. 802,856, filed June 2, 1977, now U.S. Pat. No. 4,113,500.

BACKGROUND OF THE INVENTION

1. Field of the Invention

This invention relates to a sintered apatite body, and more specifically, to a sintered apatite body having increased mechanical strength, and a process for producing an apatite powder having improved sinterability.

2. Description of the Prior Art

In recent years, ceramic materials have been superseding polymeric or metallic materials for use as medical implant materials, because ceramics are more stable in the living body than synthetic resins and metals, and are non-toxic and non-irritating. These three properties, however, are insufficient for implant materials, and a problem of affinity with the living tissues is still to be solved.

The pore sizes of conventional implant materials composed mainly of $Al_2O_3$ are controlled in order to improve their "affinity" with cells or tissues, but their chemical bondability to the living tissues is extremely poor. Accordingly, conventional implant materials should be strengthened in physical bonding by, for example, bonding more securely with a nut. Sometimes, this brings about the defect that the embedded implant is freed within the living body because of insufficient adhesion, or by a rejection of the living body.

Apatite [$Ca_5(PO_4)_3OH$], a main mineral constituent of bones and teeth, has attracted considerable attention as an implant material which remedies the defects of $Al_2O_3$-based implant materials. It has been made clear that a sintered body of apatite is an implant material having an affinity with the living body near that of living bones because of the composition and crystal structure of apatite, and it is less necessary to control the pore size of the apatite for improving its affinity with the cells or tissues.

Apatite, however, has the defect that it has poor sinterability, and a sintered body of apatite has low mechanical strength.

SUMMARY OF THE INVENTION

An object of this invention is to improve the sinterability of apatite and increase the mechanical strength of sintered apatite by adding $(Ca, Mg)_3(PO_4)_2$ to apatite.

The present invention provides a sintered body of apatite, in which the sintered body is obtained by molding and sintering a powder of apatite, [$Ca_5(PO_4)_3OH$], containing 0.01 to 20% by weight of $(Ca, Mg)_3(PO_4)_2$; and a process for producing the powder of apatite.

DETAILED DESCRIPTION OF THE INVENTION

The effect of adding $(Ca, Mg)_3(PO_4)_2$ to the apatite is to inhibit the grain growth of apatite during sintering, or to make up for the Ca-deficient portion of the apatite, thereby contributing to an increase in the mechanical strength of the sintered apatite.

The invention is described below with reference to two manufacturing processes. One process comprises adding a magnesium compound such as $Mg_3(PO_4)_2$ to a synthetic amorphous apatite powder thereby to form $Ca_5(PO_4)_3OH$ containing $(Ca, Mg)_3(PO_4)_2$. The other process comprises adding $Mg(OH)_2$ during the synthesis of the apatite, and calcining the resulting powder thereby to form $Ca(PO_4)_3OH$ containing $(Ca, Mg)_3(PO_4)_2$.

In the first process, a mixed powder of a calcium compound, a magnesium compound and amorphous apatite, $Ca_{10-x}H_x(PO_4)_6(OH)_{2-x} \cdot yH_2O$, in which $0 \leq x \leq 1$, and $y \leq x$, is used as a starting material. The amorphous apatite can be prepared using known techniques, e.g., by reacting calcium ion and phosphate ion in an aqueous solution at a pH of about 6 to about 12. The precipitate thus produced is dried to obtain the amorphous apatite. The mixed powder is calcined in an inert gas such as argon or in air at 400° to 1000° C. for about 0.1 to 2 hours. Suitable examples of starting calcium compounds which can be used include, for example, $Ca(OH)_2$, $CaCO_3$, and $CaO$. Suitable examples of starting magnesium compounds which can be used are $(Ca, Mg)_3(PO_4)_2$, $Mg_3(PO_4)_2$, $MgHPO_4$, $Mg(H_2PO_4)_2$, $MgSO_4$, $MgCO_3$, $Mg(OH)_2$, and $MgO$. The amorphous apatite is, for example, $Ca_9H(PO_4)_6OH$ when $x=1$ and $y=0$, and $Ca_5(PO_4)_3OH$ when $x=0$ and $y=0$. The materials may be mixed in the form of a powder, or a suspension e.g., in water. Basically any particle size of the powders to be mixed can be used as long as the powders can be mixed. Mixing in the form of a suspension is preferred in view of the characteristics of the resulting sintered body. The calcined powder thus obtained is compressed using, e.g., a mold press, an isostatic press, a hot press, or a hot isostatic press, etc., e.g., under pressures ranging from about 100 to about 7000 kg/cm², and then sintered in an inert gas or in air at 400° to 1700° C. for about 0.1 to 10 hours.

In the latter process, the starting material is obtained by adding incrementally a predetermined amount of $H_3PO_4$ in a suspension of $Mg(OH)_2$ and $Ca(OH)_2$ in a $Mg(OH)_2/Ca(OH)_2$ weight ratio of 0.0001:1 to 0.2:1 with thorough stirring. The starting powder is calcined, molded, and sintered under the same conditions as described above with regard to the first process.

The present invention is illustrated in greater detail below by reference to specific examples thereof. Unless otherwise indicated herein, all parts, percents, ratios and the like are by weight.

EXAMPLE 1

$Ca_3(PO_4)_2$ and $Ca(OH)_2$, both having a size less than 200 mesh, were mixed as a suspension in water in a molar ratio of 3:1, and then 0.5% by weight of $(Ca, Mg)_3(PO_4)_2$ powder as an additive was added. These components were mixed with stirring for about 1 hour at room temperature (about 10°–30° C.). After mixing, the mixture was washed with water, and dried. The resulting powder was calcined for about 1 hour in air at 900° C. Then, the calcined powder was washed with water, and dried. The resulting $Ca_5(PO_4)_3OH$ powder containing 0.5% by weight of $(Ca, Mg)_3(PO_4)_2$ was cold-pressed under a pressure of 400 kg/cm², and then sintered in air at 1300° C. for about 1 hour. X-ray diffraction analysis of this sintered structure showed that it was a pure apatite sintered body. Table 1 shows the grain sizes, the relative densities, and the compressive strengths of the sintered bodies obtained by sintering apatite powders with varying amounts of $(Ca, Mg)_3(PO_4)_2$ after calcination.

Table 1

| | Sample | | | |
|---|---|---|---|---|
| | A | B | C | D |
| Content (%) of (Ca, Mg)$_3$(PO$_4$)$_2$ in Calcined Powder | 0 | 0.1 | 0.5 | 1.0 |
| Grain Size ($\mu$) of Sintered Body | 10–25 | 5–12 | 5–15 | 5–17 |
| Relative Density (%) | 90 | 94 | 94 | 93 |
| Compressive Strength (Kg/cm$^2$) | 910 | 2000 | 1900 | 1600 |

EXAMPLE 2

To a stirred suspension of Mg(OH)$_2$ and Ca(OH)$_2$ in water with a Mg(OH)$_2$/Ca(OH)$_2$ weight ratio of 0.005:1 was added incrementally H$_3$PO$_4$ in an amount such that the molar ratio of Ca(OH)$_2$/H$_3$PO$_4$ was 1.70:1. The mixture was aged at room temperature for about 4 hours. After the ageing, the mixture was washed with water, and dried. The resulting powder was calcined in air at 900° C. for about 1 hour to produce a Ca$_5$(PO$_4$)$_3$OH powder containing 0.5% by weight of (Ca, Mg)$_3$(PO$_4$)$_2$. The calcined product was worked up in the same way as in Example 1. Table 2 shows the grain sizes, the relative densities, and the compressive strengths of the sintered bodies obtained by sintering apatite powders with varying amounts of (Ca, Mg)$_3$(PO$_4$)$_2$ after calcination.

Table 2

| | Sample | | | |
|---|---|---|---|---|
| | A | B | C | D |
| Content (%) of (Ca, Mg)$_3$(PO$_4$)$_2$ in Calcined Powder | 0 | 0.1 | 0.5 | 1.0 |
| Grain Size ($\mu$) of Sintered Body | 10–25 | 5–12 | 5–13 | 5–18 |
| Relative Density (%) | 90 | 96 | 96 | 94 |
| Compressive Strength (Kg/cm$^2$) | 910 | 2500 | 2400 | 2200 |

EXAMPLE 3

A Ca$_5$(PO$_4$)$_3$OH powder containing 0.5% of (Ca, Mg)$_3$(PO$_4$)$_2$ obtained by the same procedure as in Example 2 was placed in a high-purity alumina mold for hot pressing, and hot-pressed for 10 minutes at 1200° C. under a pressure of 200 kg/cm$^2$ to a size of 20 mm in diameter and 10 mm in height. As a result, an apatite sintered body was obtained having a very uniform quality and high mechanical strength. Table 3 shows the grain sizes, the relative densities, and the compressive strengths of the sintered bodies obtained by hot-pressing apatite powders with varying amounts of (Ca, Mg)$_3$(PO$_4$)$_2$ after calcination.

Table 3

| | Sample | | | |
|---|---|---|---|---|
| | A | B | C | D |
| Content (%) of (Ca, Mg)$_3$(PO$_4$)$_2$ in Calcined Powder | 0 | 0.1 | 0.5 | 1.0 |
| Grain Size ($\mu$) of Sintered Body | 5–9 | 3–7 | 3–9 | 3–9 |
| Relative Density (%) | 98 | 99 | 99 | 99 |
| Compressive Strength (Kg/cm$^2$) | 2500 | 3500 | 3400 | 3200 |

As can be seen from the results obtained in the above examples, the apatite powders containing (Ca, Mg)$_3$(PO$_4$)$_2$ in accordance with the present invention have very good sinterability, and can be used to produce sintered products having a very high mechanical strength, a small crystal growth, a high compressive strength and a high relative density. Accordingly, the sintered apatite bodies in accordance with this invention are useful as implant materials such as prosthetic teeth or bones.

While the invention has been described in detail and with reference to specific embodiments thereof, it will be apparent to one skilled in the art that various changes and modifications can be made therein without departing from the spirit and scope thereof.

What is claimed is:

1. A process for producing an apatite powder suitable for sintering and having the formula Ca$_5$(PO$_4$)$_3$OH, containing 0.01 to 20% by weight of (Ca, Mg)$_3$(PO$_4$)$_2$ which comprises calcining a mixed powder of 0 to 20% by weight of a calcium compound selected from the group consisting of Ca(OH)$_2$, CaCO$_3$, and CaO, 0.01 to 20% by weight of a magnesium compound selected from the group consisting of (Ca, Mg)$_3$(PO$_4$)$_2$, Mg$_3$(PO$_4$)$_2$, MgHPO$_4$, Mg(H$_2$PO$_4$)$_2$, MgSO$_4$, MgCO$_3$, Mg(OH)$_2$, and MgO, and 99.99 to 60% by weight of amorphous apatite of the formula $$Ca_{10-x}H_x(PO_4)_6(OH)_{2-x} \cdot yH_2O$$

wherein $0 \leq x \leq 1$, and $y \leq x$, whereby upon molding and sintering said apatite powder, grain-growth is inhibited thereby contributing to an increase in the mechanical strength of the sintered apatite.

2. The process of claim 1, wherein the calcining is carried out in an inert gas or in air at 400° to 1000° C. for about 0.1 to 2 hours.

3. A process for producing an apatite powder, Ca$_5$(PO$_4$)$_3$OH, containing 0.01 to 20% by weight of (Ca, Mg)$_3$(PO$_4$)$_2$ which comprises adding H$_3$PO$_4$ incrementally to a mixed suspension of Mg(OH)$_2$ and Ca(OH)$_2$ with an Mg(OH)$_2$/Ca(OH)$_2$ weight ratio of 0.0001:1 to 0.2:1, and calcining the resulting powder.

4. The process of claim 3 wherein the calcining is carried out in an inert gas or in air at 400° to 1000° C. for about 0.1 to 2 hours.

* * * * *